United States Patent
Perregaard et al.

(10) Patent No.: US 6,514,993 B1
(45) Date of Patent: Feb. 4, 2003

(54) SEROTONIN 5-HT$_{1A}$ AND DOPAMIN D$_2$ RECEPTOR LIGANDS

(75) Inventors: Jens Kristian Perregaard, Jaegerspris (DK); Ejner Knud Moltzen, Gentofte (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/424,930

(22) Filed: Dec. 9, 1996

Related U.S. Application Data

(63) Continuation of application No. PCT/DK95/00229, filed on Jun. 8, 1995.

(30) Foreign Application Priority Data

Jun. 8, 1994 (DK) ............................................... 0657/94

(51) Int. Cl.$^7$ .................. A61K 31/4439; A61K 31/454; C07D 401/06; C07D 401/08
(52) U.S. Cl. .................. 514/326; 514/341; 514/254.05; 546/207; 546/208; 546/209; 546/210; 546/274.4; 544/370
(58) Field of Search .............................. 546/274.4, 210; 514/341, 326

(56) References Cited

U.S. PATENT DOCUMENTS

| | | | |
|---|---|---|---|
| 3,374,237 A | 3/1968 | Wright, Jr. et al. | 260/268 |
| 4,452,798 A | 6/1984 | Maxwell | 424/250 |
| 5,153,206 A | * 10/1992 | Nagel | 514/326 |
| 5,698,573 A | * 12/1997 | Carling et al. | 514/326 |

FOREIGN PATENT DOCUMENTS

GB 1456253 11/1976

| | | |
|---|---|---|
| WO | WO 92/00282 | 1/1992 |
| WO | WO 93/03016 | 2/1993 |
| WO | WO 94/06768 | 3/1994 |

* cited by examiner

*Primary Examiner*—Emily Bernhardt
(74) *Attorney, Agent, or Firm*—Darby & Darby

(57) ABSTRACT

The present invention relates to a novel series of 4-phenylpiperazines, 4-phenylpiperidines and 4-phenyl-1,2,3,6-tetrahydropyridines compounds of general formula (I)

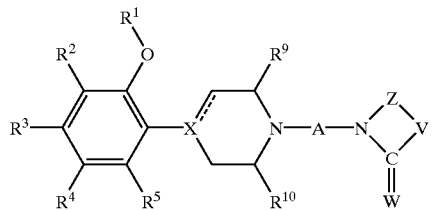

wherein A is alkylene, alkenylene, alkynylene, and $C_{3-7}$ cycloalkylene; $R^1$ is a $C_{3-10}$ alkyl, alkenyl, or alkynyl group, cycloalk(en)yl, cycloalk(en)yl-alk(en/yn)yl, trifluoromethylsulfonyl, or alkylsulfonyl, $R^2$–$R^5$ are optional substituents; $R^9$ and $R^{10}$ are hydrogen, alkyl or together form an ethylene or propylene bridge; W is O or S; V is O, S, $CR^6R^7$, or $NR^8$ wherein $R^6$, $R^7$, and $R^8$ are hydrogen or alkyl, alkenyl, cycloalkyl, cycloalkylalkyl, optionally substituted arylalkyl or aryl, or $R^6$ and $R^7$ constitute a 3–7 membered spiro ring; Z is —(CH$_2$)$_m$—, m being 2 or 3 or Z is —CH=CH—; X is N, C or CH; show effects on central serotonin 5-HT$_{1A}$ and dopamine D$_2$ receptors. Thus the novel compounds are useful in the treatment of certain psychic and neurologic disorders, in particular psychosis.

12 Claims, No Drawings

SEROTONIN 5-HT$_{1A}$ AND DOPAMIN D$_2$ RECEPTOR LIGANDS

This is a Continuation of application Ser. No. PCT/DK95/00229, filed Jun. 8, 1995.

FIELD OF INVENTION

The present invention relates to a novel series of 4-phenylpiperazines, 4-phenylpiperidines and 4-phenyl-1,2,3,6-tetrahydropyridines. Having effects on both central serotonin 5-HT$_{1A}$ and dopamine D$_2$ receptors, the novel compounds are useful in the treatment of certain psychic and neurologic disorders.

BACKGROUND OF THE INVENTION

In International patent publication No. WO 92/03426, a class of piperazine derivatives having phenyl, naphtyl or quinolyl in the 4-position and an N-aryl substituted carbamoyl alkyl group or an N-aryl substituted ureido alkyl group in the 1-position is described. Said compounds are claimed to exhibit affinity for various receptors, including 5-HT$_2$, 5-HT$_{1A}$, alpha and dopamine receptors.

EP A1 0376607 relates to certain 1-[4-(3-indolyl)butyl]-4-(2-oxyphenyl)piperazine compounds being partial 5-HT$_{1A}$ agonists.

EP A1 0526434 among a number of other compounds, describes 1-[(4-phenylpiperazin-1-yl)-C$_{2-6}$ alkyl]-benzimidazol-2-one compounds said to show 5-HT$_{1A}$ agonistic activity and 5-HT$_{2A}$ antagonistic activity.

U.S. Pat. No. 3,374,237 discloses a class of 1-phenyl-3-(4-phenyl-1-piperazinyl-C$_{2-4}$ alkyl)-2-imidazolidinones claimed to be useful as tranquilizers. No test data at all are presented. FR Patents Nos 1.394.708 and 1.513.604, respectively, describe similar compounds without a phenyl substituent in the 4-position of the piperazinyl group and said to possess tranquilizing and psychopharmachodynamic properties, respectively.

AU Patent No 15658/83 discloses 3-(4-phenyl-1-piperazinyl-C$_{2-4}$ alkyl)hydantoin compounds having antihypertensive effects.

WO 92/00282 relates to a subgroup of the compounds of U.S. Pat. No. 3,374,237 which are 1-phenyl-3-[4-(4-phenyl-1-piperazinyl)-1-butyl]-2-imidazolidinones having an optional chloro atom in the 2-position of the phenyl substituent in 1-position of the imidazolidinone ring and a methoxy or ethoxy substituent in the 2- and/or 3-position of the other phenyl substituent. The compounds show dopaminergic effects.

Clinical studies of known 5-HT$_{1A}$ partial agonists such as e.g. buspirone, 8-[4-[4-(2-pyrimidyl)-1-piperazinyl]butyl]-8-azaspiro[4,5]decane-7,9-dione, gepirone, 4,4-dimethyl-1-[4-[4-(2-pyrimidyl)-1-piperazinyl]butyl]-2,6-piperidinedione, and ipsapirone, 2-[4-[4-(2-pyrimidyl)-1-piperazinyl]butyl]-1,2-benzothiazol-3(2H)-one-1,1-dioxide, have shown that 5-HT$_{1A}$ partial agonists are useful in the treatment of anxiety disorders such as generalised anxiety disorder, panic disorder, and obsessive compulsive disorder (Glitz, D. A., Pohl, R., *Drugs* 1991, 41, 11). Preclinical studies indicate that also full agonists are useful in the treatment of the above mentioned anxiety related disorders (Schipper, *Human Psychopharmacol.*, 1991, 6, S53).

There is also evidence, both clinical and preclinical, in support of the beneficial effect of 5-HT$_{1A}$ agonists in the treatment of depression, impulse control disorders and alcohol abuse (van Hest, *Psychopharmacol.*, 1992, 107, 474; Schipper et al, *Human Psychopharmacol.*, 1991, 6, S53; Cervo et al, *Eur. J. Pharmacol.*, 1988, 158, 53; Glitz, D. A., Pohl, R., *Drugs* 1991, 41, 11; Grof et al., *Int. Clin.Psychopharmacol.* 1993, 8, 167–172; Ansseau et al., *Human Psychopharmacol.* 1993, 8, 279–283).

5-HT$_{1A}$ agonists and partial agonists inhibit isolation-induced aggression in male mice indicating that these compounds are useful in the treatment of aggression (Sanchez et al., *Psychopharmacology*, 1993, 110, 53–59).

Furthermore, 5-HT$_{1A}$ agonists have been reported to show antipsychotic effect in animal models (Wadenberg and Ahlenius, *J. Neural. Transm.*, 1991, 83, 43; Ahlenius, *Pharmacol.&Toxicol.*, 1989, 64, 3; Lowe et al., *J. Med. Chem.*, 1991, 34, 1860; New et al., *J. Med. Chem.*, 1989, 32, 1147; and Martin et al., *J. Med. Chem.*, 1989, 32, 1052) and recent studies also indicate that 5-HT$_{1A}$ receptors are important in the serotonergic modulation of haloperidol-induced catalepsy (Hicks, *Life Science* 1990, 47, 1609, Wadenberg et al. *Pharmacol. Biochem. & Behav.* 1994, 47, 509–513) suggesting that 5-HT$_{1A}$ agonists are useful in the treatment of the extrapyramidal side effects (EPS) induced by conventional antipsychotic agents such as haloperidol.

Damping of dopamine (DA) overactivity by the use of DA receptor blocking drugs is today the most important principle in the treatment of schizophrenia, in particular the positive symptoms thereof, and other psychoses. "Classical neuroleptics" such as haloperidol, cis(Z)-flupentixol and chlorpromazine are believed to induce antipsychotic effect via DA receptor blockade. Unfortunately, these classical neuroleptics also induce EPS, which seem to be correlated to the propensity of these compounds to induce catalepsy in rodents (Arnt et al. *Neuropharmacology*, 1981, 20, 1331–1334). A combination of 5-HT$_{1A}$ receptor agonism which may prevent EPS in man (cf. above) and dopamine receptor blockade to treat the positive symptoms of schizophrenia would thus be very advantageous.

Furthermore, 5-HT$_{1A}$ agonists have shown neuroprotective properties in rodent models of focal and global cerebral ischaemia and may, therefore, be useful in the treatment of ischaemic disease states (Prehn, *Eur. J. Pharm.* 1991, 203, 213).

Pharmacological studies have been presented which indicate that 5-HT$_{1A}$ antagonists are useful in the treatment of senile dementia (Bowen et al, *Trends Neur. Sci.* 1992, 15, 84).

Both in animal models and in clinical trials, it has been shown that 5-HT$_{1A}$ agonists exert antihypertensive effects via a central mechanism (Saxena and Villalón, *Trends Pharm. Sci.* 1990, 11, 95; Gillis et al, *J. Pharm. Exp. Ther.* 1989, 248, 851. 5-HT$_{1A}$ ligands may, therefore, be beneficial in the treatment of cardiovascular disorders.

Accordingly, agents acting both on the 5-HT$_{1A}$ receptor, including agonists, partial agonists and antagonists, and at the same time blocking the dopamine D$_2$ receptor are believed to be of potential use in the therapy of such conditions, in particular in the treatment of psychosis, and thus being highly desired.

SUMMARY OF THE INVENTION

It has now been found that a novel series of phenylpiperazines, 4-phenylpiperidines and 4-phenyl-1,2,3,6-tetrahydropyridines posseses both central serotonergic 5-HT$_{1A}$ and antidopaminergic D$_2$ activity.

Accordingly, the present invention relates to novel 4-phenylpiperazine, 4-phenylpiperidine and 4-phenyl-1,2,3,6-tetrahydropyridine compounds of general Formula I:

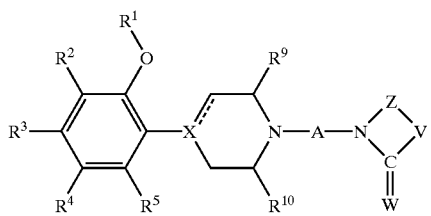

wherein A is a spacer group selected from branched or straight chain $C_{3-8}$ alkylene, $C_{3-8}$ alkenylene and $C_{3-8}$ alkynylene, and $C_{3-7}$ cycloalkylene, said spacer group being optionally substituted with lower alkyl, aryl or hydroxy;

$R^1$ is a branched $C_{3-10}$ alkyl, $C_{3-10}$ alkenyl or $C_{3-10}$ alkynyl group, cycloalk(en)yl, cycloalk(en)yl-lower alk(en/yn)yl, trifluoromethylsulfonyl, or lower alkylsulfonyl, $R^2$–$R^5$ are independently selected from the group consisting of hydrogen, halogen, lower alkyl, lower alkoxy, lower alkylthio, hydroxy, lower alkylsulfonyl, cyano, lower alkylcarbonyl, phenylcarbonyl, halogen substituted phenylcarbonyl, trifluoromethyl, trifluoromethylsulfonyloxy, cycloalkyl, cycloalkyl-lower alkyl, nitro, lower alkylamino, di-lower-alkylamino and trifluoromethylthio;

$R^9$ and $R^{10}$ are independently hydrogen, lower alkyl or they may be linked together, thereby forming an ethylene or propylene bridge;

W is O or S;

V is O, S, $CR^6R^7$, or $NR^8$ wherein $R^6$, $R^7$, and $R^8$ are independently chosen among hydrogen or lower alkyl or lower alkenyl, cycloalkyl, cycloalkyl-lower-alkyl, aryl-lower-alkyl or aryl, or $R^6$ and $R^7$ are linked together to constitute a 3–7 membered spirojoined ring;

Z is —$(CH_2)_m$—, m being 2 or 3 or Z is —CH═CH—;

the dotted line, emanating from X, indicates an optional bond and when it does not indicate a bond X is N or CH and when it indicates a bond X is C;

any alkyl, cycloalkyl or cycloalkylalkyl group present being optionally substituted with one or two hydroxy groups, which again are optionally esterified with an aliphatic or aromatic carboxylic acid; and any aryl substituent present being optionally substituted with halogen, lower alkyl, lower alkoxy, lower alkylthio, hydroxy, lower alkylsulfonyl, cyano, acyl, trifluoromethyl, trifluoromethylsulfonyloxy, cycloalkyl, cycloalkylalkyl or nitro;

and pharmaceutically acceptable acid addition salts thereof.

The compounds of the invention have affinity for the 5-HT$_{1A}$ receptor and the dopamin $D_2$ receptor in vitro and they show 5-HT$_{1A}$ agonistic or antagonistic as well as dopaminergic activity in vivo. Furthermore, the compounds lack cataleptogenic effect or are only weakly cataleptogenic in rats indicating a very low potential for inducing EPS in man. Accordingly, the compounds of the invention are considered useful as drugs for the treatment of psychosis, positive symptoms of schizophrenia, anxiety disorders, such as generalised anxiety disorder, panic disorder, and obsessive compulsive disorder, depression, impulse control disorders, alcohol abuse, aggression, EPS induced by conventional antipsychotic agents, ischaemic disease states, senile dementia and cardiovascular disorders.

In another aspect, the invention provides a pharmaceutical composition comprising at least one novel 4-phenylpiperazine, 4-phenylpiperidine or 4-phenyl-1,2,3,6-tetrahydropyridine according to the invention as defined above or a pharmaceutically acceptable acid addition salt or prodrug thereof in a therapeutically effective amount and in combination with one or more pharmaceutically acceptable carriers or diluents.

In a further aspect, the present invention provides the use of a 4-phenylpiperazine, 4-phenylpiperidine or 4-phenyl-1,2,3,6-tetrahydropyridine compound according to the invention or an acid addition salt or prodrug thereof for the manufacture of a pharmaceutical preparation for the treatment of the above mentioned disorders and diseases.

DETAILED DESCRIPTION OF THE INVENTION

Some of the compounds of general Formula I may exist as optical isomers thereof and such optical isomers are also embraced by the invention.

Prodrugs of the compounds of general Formula I are also embraced by the invention.

The term cycloalkyl designates a carbocyclic ring having 3–8 carbon atoms, inclusive, or a bicyclic or tricyclic carbocycle, such as adamantyl, and cycloalkenyl designate corresponding groups containing an unsaturated bond.

The term lower alkyl refers to branched or unbranched alkyl groups having from one to six carbon atoms inclusive. Examples of such groups are methyl, ethyl, 1-propyl, 2-propyl, 1-butyl, 2-butyl, 2-methyl-2-propyl and 2-methyl-1-propyl. Accordingly, the terms lower alkoxy, lower alkylthio, lower alkylsulfonyl, lower alkylcarbonyl and lower alkylamino refer to such groups in which the alkyl moiety is a lower alkyl group as defined above, such as methoxy, ethoxy, 1-propoxy, methylthio, ethylthio, 1-propylthio, 2-propylthio, methylsulfonyl, ethylsulfonyl, etc. Similarly, lower alkenyl and alkynyl, respectively, designate such groups having from two to six carbon atoms, inclusive. Preferred lower alkyl, alkenyl and alkynyl groups are those having up to four carbon atoms.

The term aryl refers to a mono- or bicyclic carbocyclic or heterocyclic aromatic group, such as phenyl, indolyl, thienyl, pyrimidyl, oxazolyl, isoxazolyl, thiazolyl, isothiazolyl, imidazolyl, benzofuranyl, benzothienyl, pyridyl, naphthyl, and furanyl, in particular phenyl, pyrimidyl, indolyl, and thienyl.

Halogen means fluoro, chloro, bromo or iodo.

Acyl refers to an arylcarbonyl, $C_{1-18}$ alkylcarbonyl, N'—$(C_{1-18})$alkyl- or N',N'-di$(C_{1-18})$-alkylcarbonyl group.

The expression alk(en/yn)yl means that the group may be an alkyl, alkenyl, or alkynyl group.

In Formula I, A is preferably a —$(CH_2)_n$— group wherein n is an integer of 3–8, inclusive, more preferably 4–6, inclusive. Most preferably n is 4.

$R^1$ is preferably branched $C_{3-6}$ alkyl, cycloalkyl, cycloalkyl-lower alkyl or trifluoromethylsulfonyl, more preferably 2-propyl, 2-methyl-1-propyl, 2-butyl, 3-pentyl, 2,2-dimethyl-1-propyl, tert-butyl, cyclopropylmethyl, cyclopentyl, 2,4-dimethyl-3-pentyl or trifluoromethylsulfonyl, in particular 2-propyl, cyclopentyl, cyclopropylmethyl or trifluoromethylsulfonyl.

$R^2$–$R^5$ are preferably hydrogen, halogen or cyano and more preferably they are all hydrogen or one of the substituents is halogen and the others are hydrogen. $R^9$ and $R^{10}$ are preferably both hydrogen.

Z is preferably —CH$_2$CH$_2$— or —CH=CH— and V preferably designates N—R$^8$, wherein R$^8$ is lower alkyl, cycloalkyl, phenyl or phenyl substituted with halogen, most preferably cyclohexyl, adamantyl, isopropyl or 4-fluorophenyl. W is preferably oxygen.

Preferred compounds are:
- 3-Cyclohexyl-1-[4-[4-[2-(2-propyloxy)phenyl]-1-piperazinyl]butan-1-yl]-2-imidazolidinone.
- 3-(4-Fluorophenyl)-1-[4-[4-[2-(2-propyloxy)phenyl]-1-piperazinyl]butan-1-yl]-2-imidazolidinone.
- 3-Cyclohexyl-1-[4-[4-(2-cyclopentyloxyphenyl)-1-piperazinyl]butan-1-yl]-2-imidazolidinone.
- 1-[4-[4-(2-Cyclopentyloxyhenyl)-1-piperazinyl]butan-1-yl]-3-(4-fluorophenyl)-2-imidazolidinone.
- 1-[3-[4-[2-(2-Propyloxy)phenyl]-1-piperazinyl]-1-propyl]-3-phenyl-2-imidazolidinone.
- 3-(4-Fluorophenyl)-1-[4-[4-[2-(2-propyloxy)phenyl]-1-piperidinyl]butan-1-yl]-2-imidazolidinone.
- 3-Cyclohexyl-1-[4-[4-[2-(2-propyloxy)phenyl]-1-piperidinyl]butan-1-yl]-2-imidazolidinone.
- 3-Cyclohexyl-1-[3-[4-[2-(2-propyloxy)phenyl]-1-piperidinyl]-1-propyl]-2-imidazolidinone.
- 3-(2-Propyl)-1-[4-[4-[2-(2-propyloxy)phenyl]-1-piperidinyl]-1-butyl]-2-imidazolidinone.
- 3-Cyclohexyl-1-[6-[4-[2-(2-propyloxy)phenyl]-1-piperidinyl]hexan-1-yl]-2-imidazolidinone.
- 3-Cyclohexyl-1-[4-[4-(2-cyclopropylmethyloxyphenyl)-1-piperidinyl]butan-1-yl]-2-imidazolidinone.
- 3-Cyclohexyl-1-[4-[4-[2-(2,2-dimethylpropyloxy)phenyl]-1-piperidinyl]butan-1-yl]-2-imidazolidinone.
- 3-Cyclohexyl-1-[4-[4-[2-(2-propyloxy)phenyl]-1-piperidinyl]butan-1-yl]-1,3-dihydroimidazol-2-one.
- 3-(1-Adamantyl)-1-[4-[4-[2-(2-propyloxy)phenyl]-1-piperidinyl]butan-1-yl]-1,3-dihydroimidazol-2-one.
- 3-(4-Fluorophenyl)-1-[4-[4-[2-(2-trifluoromethylsulfonyloxy)phenyl]-1-piperazinyl]butan-1-yl]-2-imidazolidinone.
- 3-Cyclohexyl-1-[4-[4-[2-(2-trifluoromethylsulfonyloxy)phenyl]-1-piperazinyl]butan-1-yl]-2-imidazolidinone.
- 3-(4-Fluorophenyl)-1-[4-[4-[2-(2-trifluoromethylsulfonyloxy)phenyl]-1-piperidinyl]butan-1-yl]-2-imidazolidinone.
- 3-Cyclohexyl-1-[4-[4-[2-(2-propyloxy)phenyl]-1,2,3,6-tetrahydropyridin-1-yl]butan-1-yl]-2-imidazolidinone.
- 3-(4-Fluorophenyl)-1-[4-[4-[2-(2-propyloxy)phenyl]-1,2,3,6-tetrahydropyridin-1-yl]butan-1-yl]-2-imidazolidinone.
- 3-Cyclohexyl-1-[4-[4-[2-(cyclopropylmethoxy)phenyl]-1,2,3,6-tetrahydropyridin-1-yl]butan-1-yl]-2-imidazolidinone.
- 3-Cyclohexyl-1-[4-[4-[2-(2-propyloxy)phenyl]-1,2,3,6-tetrahydropyridin-1-yl]butan-1-yl]-2,3-dihydroimidazol-2-one.
- 3-(1-Adamantyl)-1-[4-[4-[2-(2-propyloxy)phenyl]-1,2,3,6-tetrahydropyridin-1-yl]butan-1-yl]-2,3-dihydroimidazol-2-one.
- 3-Cyclohexyl-1-[4-[4-[2-(1,1-dimethylethyl)oxy)phenyl]-1-piperidinyl]butan-1-yl]-2-imidazolidinone.
- 3-Cyclohexyl-1-[4-[4-[2-cyclopropyloxyphenyl)-1-piperidinyl]butan-1-yl]-2-imidazolidinone.
- 3-Cyclopentyl-1-[3-[4-[2-(2-propyloxy)phenyl]-1-piperidinyl]butan-1-yl]-2-imidazolidinone.
- 3-Cyclohexyl-1-[4-[4-[5-fluoro-2-(2-propyloxy)phenyl]-1-piperidinyl]butan-1-yl]-2-imidazolidinone.
- 3-Cyclohexyl-1-[4-[4-[4-chloro-2-(2-propyloxy)phenyl]-1-piperidinyl]butan-1-yl]-2-imidazolidinone.
- 3-Cyclohexyl-1-[4-[4-[5-bromo-2-(2-propyloxy)phenyl]-1-piperidinyl]butan-1-yl]-2-imidazolidinone.
- 3-Cyclohexyl-1-[4-[4-[5-cyano-2-(2-propyloxy)phenyl]-1-piperidinyl]butan-1-yl]-2-imidazolidinone.
- 3-Adamantyl-1-[4-[4-[2-(2-propyloxy)phenyl]-1-piperidinyl]butan-1-yl]-2-imidazolidinone.
- 3-Cyclohexyl-1-[4-[4-[2-(2,4-dimethyl-3-pentyloxy)phenyl]-1-piperidinyl]butan-1-yl]-2-imidazolidinone.

The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions methods well known in the art may be used, and any pharmaceutically acceptable carriers, diluents, exipients, or other additive usually used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

The invention moreover relates to a method for the preparation of the novel 4-phenylpiperazines, 4-phenylpiperidines and 4-phenyl-1,2,3,6-tetrahydropyridines of Formula I, comprising:

a) reacting a compound of Formula II with a compound of Formula III:

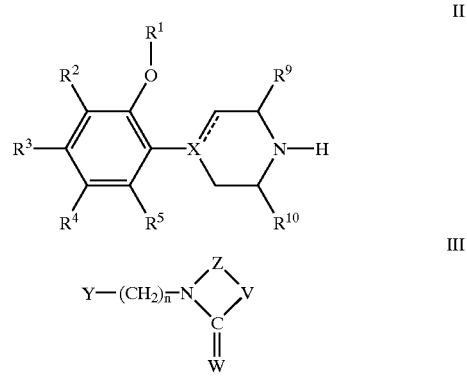

wherein R$^1$–R$^5$, R$^9$, R$^{10}$, X, V, W, Z, n, and the dotted line are as previously defined and Y is a suitable leaving group such as halogen, mesylate, or tosylate; or b) reducing the amide carbonyl of a compound of Formula IV:

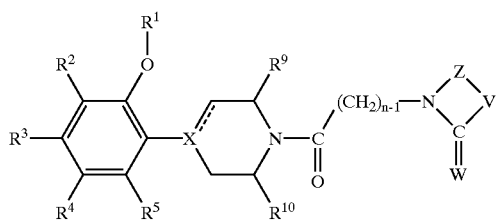

IV wherein $R^1$–$R^5$, $R^9$, $R^{10}$, X, V, W, Z, n, and the dotted line are as previously defined; or c) reacting a compound of Formula V:

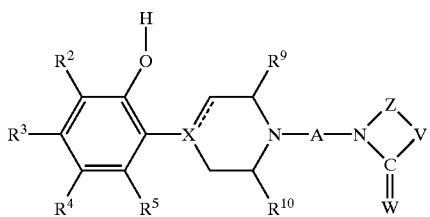

V wherein $R^2$–$R^5$, $R^9$, $R^{10}$, X, V, W, Z, A and the dotted line are as previously defined with a compound $R^1Y$ wherein $R^1$ is as previously defined and Y is a suitable leaving group such as halogen, mesylate, or tosylate; or d) reductive alkylation of the NH group of a compound of the Formula VI:

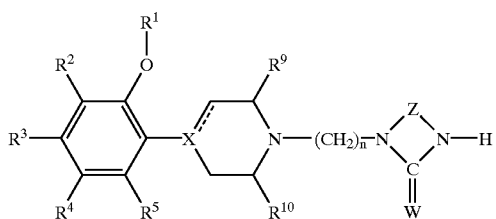

VI wherein $R^1$–$R^5$, $R^9$, $R^{10}$, X, V, W, Z, A and the dotted line are as previously defined, with and aldehyde R'CHO, a ketone R"R'"CO or a carboxylic acid R' COOH in which formulas R', R" and R'" are groups which together with the nitrogen atom form N—CH$_2$R' and N—CHR"R'" groups, respectively, which are embraced by the previous definition of V; or e) reducing the double bond of the 1,2,3,-6-tetrahydropyridine derivative of Formula VII:

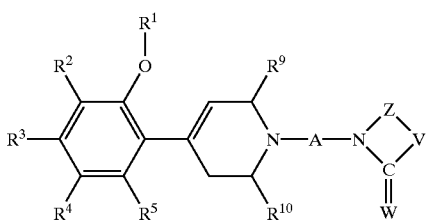

VII wherein $R^1$–$R^5$, $R^9$, $R^{10}$, X, V, W, Z and A are as previously defined;

whereupon the compound of Formula I is isolated as the free base or a pharmaceutically acceptable acid addition salt thereof.

The reaction of a compound of Formula II with a compound of Formula III according to Method a) is performed in a suitable organic solvent such as acetone, methyl isobutyl ketone, ethanol, 2-propanol, N-methyl-2-pyrrolidinone, preferably at an elevated temperature, eg. at the boiling point of the solvent, and generally in the presence of a base (such as potassium carbonate or triethylamine).

The reduction according to Method b) is conveniently performed by use of LiAlH$_4$, AlH$_3$ or diborane in an inert solvent such as tetrahydrofuran, dioxane, or diethyl ether at room temperature or at a slightly elevated temperature.

The reaction of a phenol compound of Formula V according to Method c) is generally performed by initially generating the phenolate ion by addition of a strong base (eg. potassium tert-butoxide) in an inert solvent such as diethyl ether, tetrahydrofuran, toluene, or dimethoxyethane preferably at room temperature or below. The phenolate ion is subsequently reacted with the compound of formula $R^1Y$ at an elevated temperature, eg. at the boiling point of the solvent. Trifluoromethylsulfonyloxy derivatives are conveniently obtained by triflation (see methods in WO 93/11761 Patent publication) of the properly substituted phenols of Formula V. Triflic acid anhydride, N-phenyltrifluoromethanesulfonimide, and triflic acid chloride are preferred as triflating agents.

The reductive alkylation of a compound of Formula VI according to Method d) is generally performed under acidic conditions, eg. in acetic acid, using NaBH$_4$, NaCNBH$_3$ or catalytic (Pt or Pd as catalysts) hydrogenation. Temperatures are generally at room temperature or below.

The reduction of a tetrahydropyridinyl double bond of a compound of Formula VII according to Method e) is generally performed by catalytic hydrogenation at low pressure (<3 atm.) in a Parr apparatus, or by using a reducing agent such as diborane in an inert solvent such as tetrahydrofuran, dioxane, or diethyl ether.

The 1-Unsubstituted 4-arylpiperazines of Formula II (X=N) are either commercially available or may be synthesized from the corresponding anilines and N',N'-bis(2-chloroethyl)amine by refluxing in highboiling solvents as eg. chlorobenzene typically for some days (2–3) according to methods described in Martin et al. *J. Med. Chem.* 1989, 32 1052–1056.

The 4-Phenylpiperidines of Formula II (X=CH) are either commercially available or prepared as described in eg. U.S. Pat. No. 2,891,066; McElvain et al. *J.Amer.Chem. Soc.* 1950, 72, 3134; Bally et al *Chem.Ber.* 1887, 20, 2590. The corresponding 4-phenyl-1,2,3,6-tetrahydropyridines of Formula II (X=C) are prepared from N-protected 4-piperidones by addition of properly substituted phenyl lithium or phenyl magnesium halides followed by acid catalyzed water elimination. The N-protecting group (carbamate, benzyl, sulfonyl, acetyl) is finally removed in a conventional manner.

The synthesis of more specific compounds of Formula II are given in detail in the Experimental Section.

1-(3-Chloropropyl)-, 1-(4-chlorobutyl)-, 1-(5-chloropentyl)-, and 1-(6-chlorohexyl)-2-imidazolidinones or the corresponding 3-substituted 2-imidazolidinones were prepared according to methods in Perregaard et al. *J.Med.Chem.* 1992, 35, 1092–1101 or references cited therein, or the detailed methods are described below.

EXPERIMENTAL SECTION

In the following, the invention is further illustrated by examples which, however, may not be construed as limiting.

9

In all examples, melting points were determined on a Büchi SMP-20 apparatus and were unadjusted. $^1$H NMR spectra were recorded at 250 MHz on a Bruker AC 250 spectrometer. Deuterated chloroform (99.8% D) or dimethylsulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, p=pentet, h=heptet, dd=double doublet, dt=double triplet, dq=double quartet, qui=quintet of triplets, m=multiplet.

EXAMPLE 1 (Analogous to Method d)

1-(4-Chloro-1-butyl)-3-cyclohexyl-2-imidazolidinone 1a

A mixture of 1-(4-chloro-1-butyl)-2-imidazolidinone (50 g) and cyclohexanone (83.3 g) in glacial acetic acid (1000 ml) was stirred for one hour at room temperature. The mixture was cooled to 10–15° C. and NaBH$_4$ (42.4 g) was added in small portions during 5 hours. After stirring overnight at room temperature, acetic acid was evaporated in vacuo. Water (500 ml) and dichloromethane (300 ml) were added and pH adjusted to >9 by addition of aqueous diluted NH$_4$OH. The organic phase was separated, dried with anhydrous MgSO$_4$, filtered and the solvent evaporated in vacuo. The remaining crude product was purified by column chromatography on silica gel (eluted with ethyl acetate). The pure title compound 1a crystalized upon standing. Yield: 33 g, mp: 30–35° C.

In a corresponding manner the following imidazolidinones were prepared:

1-(3-Chloro-1-propyl)-3-cyclohexyl-2-imidazolidinone 1b.

1-(4-Chloro-1-butyl)-3-isopropyl-2-imidazolidinone, 1c.

1-(6-Chloro-1-hexyl)-3-cyclohexyl-2-imidazolidinone, 1d.

EXAMPLE 2

1-(4-Chloro-1-butyl)-3-(4-fluorophenyl)-2-imidazolidinone 2a

To 2-aminoethanol (1100 g) in ethanol (1000 ml) was added 4-chlorobutanol (220 g). The mixture was refluxed for 4 hours. After cooling to 10° C., sodium methoxide in methanol (380 ml) was added. The precipitate was filtered off and volatile material was evaporated in vacuo. The remaining oil was distilled at reduced pressure. 4-[N-(2-hydroxyethyl)amino]butanol was collected at 135–140° C. at 0.2–0.4 mmHg. Yield: 106 g. The aminoalcohol (25 g) was dissolved in dichloromethane (150 ml) and a solution og 4-fluorophenylisocyanate (26 g) in dichloromethane (25 ml) was added dropwise at 0–8° C. After reflux for 2 hours the solvent was evaporated in vacuo leaving the crude 1-(2-hydroxyethyl)-1-(4-hydroxybutyl)-3-(4-fluorophenyl)urea as an oil. Yield: 56 g. To a solution of all of the crude urea derivative and N,N-dimethylformamide (DMF, 1 ml) in dichloromethane (250 ml) was added dropwise a solution of thionylchloride (40 ml) in dichloromethane (60 ml) at 10–20° C. The mixture was refluxed for 3 hours. Volatile material was evaporated in vacuo. This remaining material was heated at 130–150° C. for 2 hours. Dichloromethane (50 ml) was added and the mixture was directly filtered through silica gel (eluted with a 1:1 mixture of ethyl acetate and heptane). The title compound 2a crystallized upon evaporation of the solvents. Yield: 33 g, mp : 62–64° C.

10

In a corresponding manner the following imidazolidinone was prepared:

1-(3-Chloro-1-propyl)-3-phenyl-2-imidazolidinone 2b.

EXAMPLE 3

4-(3-Cyclohexyl-1,3-dihydroimidazol-2-on-1-yl)-1-butyl methanesulfonate, 3a

A mixture of 4-butyrolactone (54 g) and aminoacetaldehyde dimethylacetal (55 g) in tetrahydrofuran (THF) (500 mL) was refluxed for 4 h. A further portion of aminoacetaldehyde dimethylacetal (27 g) was added followed by reflux for 2 h. Reflux was continued and two further portions of acetal were added at 2 h intervals. Concentration of the reaction mixture in vacuo followed by destillation of the remaining oil gave N-(2,2-dimethoxyethyl)-4-hydroxybutyramide as an oil, bp. 230° C./10 torr, yield 72 g. The oil was dissolved in dry THF (800 mL) and added slowly to a suspension of of lithium aluminium hydride in THF (200 mL). After reflux for 16 h, the reaction mixture was cooled and subsequently quenched with water (88 mL), 15% NaOH solution (44 mL), and water (220 mL). Filtration and removal of solvent in vacuo gave an oil which was dissolved in methylene chloride (500 mL) and dried over magnesium sulfate. Filtration and removal of solvent in vacuo gave 4-(2,2-dimethoxyethylamino)-1-butanol as an oil, yield 62 g. A portion of the oil (20 g) was dissolved in methylene chloride (100 mL) and added dropwise to a solution of cyclohexylisocyanate in methylene chloride (50 mL) at 5° C. Reflux for 3 h and concentration in vacuo gave N-cyclohexyl-N'-(2,2-dimethoxyethyl)-N'-(4-hydroxy-1-butyl)urea as an oil, yield 35 g. The oil was dissolved in a mixture of THF (200 mL) and 2 M hydrochloric acid (200 mL) followed by reflux for 24 h. The reaction mixture was concentrated in vacuo followed by addition of ethyl acetate (300 mL) and 4 M NaOH (300 mL). The organic phase was dried over magnesium sulfate. Removal of solvent gave 1-cyclohexyl-3-(4-hydroxy-1-butyl)-1,3-dihydroimidazol-2-one as an oil, yield 29 g. The oil was dissolved in methylene chloride (250 mL) and triethylamine (13 g) was added followed by cooling to 5° C. A solution of methanesulfonyl chloride (14 g) in methylene chloride (20 mL) was added dropwise followed by stirring for 1.5 h at room temperature. The reaction mixture was washed with water, dried over magnesium sulfate and concentrated in vacuo giving the title compound as an oil, yield 36 g. $^1$H NMR (CDCl$_3$): δ 1.05–1.25 (m, 1H), 1.30–1.50 (m, 4H), 1.60–2.00

(m, 9H), 3.00 (s, 3H), 3.65 (t, 2H), 3.85–4.05 (m, 1H), 4.25 (t, 2H), 6.20 (d, 1H), 6.25 (d, 1H).

In a corresponding manner the following 1,3-dihydroimidazol-2-one was prepared:

4-[3-(1-Adamantyl)-1,3-dihydroimidazol-2-on-1-yl]-1-butyl methanesulfonate, 3b.

EXAMPLE 4 (Method a)

3-Cyclohexyl-1-[4-[4-[2-(2-propyloxy)phenyl]-1-piperazinyl]butan-1-yl]-2-imidazolidinone, Oxalate 4a A mixture of 1-[2-(2-propyloxy)phenyl]piperazine (5.0 g), 1-(4-chloro-1-butyl)-3-cyclohexyl-2-imidazolidinone 1a (3.0 g), a crystal of potassium iodide, and potassium carbonate (4.0 g) in methyl isobutyl ketone (MIBK) (100 ml) was refluxed for 16 hours. Inorganic salts were filtered off while still hot. After cooling to room temperature, the crude reaction mixture was filtered through silica gel (eluted with a 1:1 mixture of ethyl acetate and methanol). After evaporation of the solvents 3.9 g of crude product was left as a viscous oil. The oxalate salt crystallized from acetone. Yield: 2.4 g, mp: 133–134° C. $^1$H NMR (DMSO-$d_6$) δ 1.00–1.80 (m, 14H); 1.25 (h, 6H); 2.85–3.30 (m, 16H); 3.35–3.55 (m, 1H); 4.60 (h, 1H); 6.80–7.00 (m, 4H).

In a similar way the following compounds were prepared:

3-(4-Fluorophenyl)-1-[4-[4-[2-(2-propyloxy)phenyl]-1-piperazinyl]butan-1-yl]-2-imidazolidinone 4b, mp: 135–137° C. (ethyl acetate). $^1$H NMR (CDCl$_3$) δ 1.45 (d, 6H); 1.60 (t, 4H); 2.45 (t, 2H); 2.65 (broad s, 4H); 3.15 (broad s, 4H); 3.35 (t, 2H); 3.50 (t, 2H); 3.80 (t, 2H); 4.60 (h, 1H); 6.85–7.00 (m, 4H); 7.05 (t, 2H); 7.50 (dd, 2H).

3-Cyclohexyl-1-[4-[4-(2-cyclopentyloxyphenyl)-1-piperazinyl]butan-1-yl]-2-imidazolidinone, dihydrochloride 4c, mp: 182–193° C. (acetone). $^1$H NMR (DMSO-$d_6$) δ 1.05–2.00 (m, 22H); 3.05–3.20 (m, 8H); 3.40–3.55 (m, 5H); 4.85 (qui, 1H); 6.85–7.00 (m, 4H); 7.60 (broad s, 1H); 11.05 (broad s, 1H).

1-[4-[4-(2-Cyclopentyloxyphenyl)-1-piperazinyl]butan-1-yl]-3-(4-fluorophenyl)-2-imidazolidinone, 4d, mp: 111–116° C. (acetone). $^1$H NMR (CDCl$_3$) δ 1.60–1.95 (m, 12H); 2.40 (broad t, 2H); 2.65 (broad s, 4H); 3.05 (broad s, 4H); 3.25 (broad t, 2H); 3.45 (t, 2H); 3.75 (t, 2H); 4.80 (qui, 1H); 6.80–7.05 (m, 6H); 7.45 (dd, 2H).

1-[3-[4-(2-(2-propyloxy)phenyl]-1-piperazinyl]-1-propyl]-3-phenyl-2-imidazolidinone, 4e, mp: 167–68° C. (ethanol). $^1$H NMR (CDCl$_3$) δ 1.25 (d, 6H), 1.75 (qui, 2H), 2.60 (t, 2H), 2.75 (m, 4H), 3.05 (m, 4H), 3.25 (t, 2H), 3.45 (t, 2H), 3.80 (t, 2H), 4.60 (h, 1H), 6.60 (s, 3H), 6.80–6.95 (m, 4H), 7.00 (t, 1H), 7.30 (t, 2H), 7.55 (d, 2H).

EXAMPLE 5

1-(tert-Butyloxycarbonyl)-4-(2-hydroxyphenyl)piperidine 5a

2-Methoxybenzaldehyde (200 g) and ethyl acetoacetate (400 g) were mixed and cooled to 5° C. Piperidine (25 ml) was added and the mixture was stirred overnight at room temperature. The next day potassium tert-butoxide (25 g) was added. After 1.5 hours the mixture totally solidified and was left for 2 days. Ethanol (2000 ml) was added and the pricipitate was filtered off, washed with ethanol and finally dried in vacuo. Yield: 326 g. All of the thus obtained solid product (325 g) was added in small portions during one hour to a solution of potassium hydroxide (260 g) in water (320 ml) kept at 80–90° C. After stirring for further two hours at 80°, water (2000 ml) and diethyl ether (1000 ml) were added. After stirring, the organic phase was separated and discarded. To the remaining aqueous solution was added ice and concentrated hydrochloric acid until pH<1. After stirring for 45 minutes, the precipitated product was filtered off and dried. Yield of 3-(2-methoxyphenyl)-1,5-pentanedicarboxylic acid: 137 g, mp: 183–185° C. A mixture of the pentane-dicarboxylic acid (97 g) and urea (28 g) was heated at 160–165° C. for 2 hours. After cooling to 70° C., ethanol (150 ml) was added. The precipitated 4-(2-methoxyphenyl)-2,6-piperidinedione was filtered off and subsequently dried. Yield 66 g. Mp: 127–129° C. To a suspension of LiAlH$_4$ (30 g) in dry THF (1000 ml) were added small portions (in total 65 g) of the piperidinedione while the temperature gradually raised to reflux. After reflux for 2.5 hours, the mixture was cooled below 10° C. and diluted aqueous NaOH solution (4M) (60 ml) was cautiously added. Precipitated inorganic salts were filtered off. The solvent was evaporated and the remaining oil was dissolved in dichloromethane, dried (anh. Na$_2$SO$_4$), filtered and dichloromethane evaporated leaving 56 g of 4-(2-methoxyphenyl)piperidine as an oil. All of the piperidine was dissolved in a mixture of 48% aqueous hydrobromic acid (400 ml) and a 33% solution of hydrogenbromide in acetic acid (400 ml). The solution was refluxed for 19 hours. Excess hydrobromic and acetic acids was evaporated in vacuo leaving 47 g of 4-(2-hydroxyphenyl)piperidine hydrobromide as a viscous oil. The hydrobromide (45 g) was dissolved in a mixture of water (300 ml) and THF (150 ml). Potassium carbonate (80 g) was added in small lots. A solution of di-tert-butyldicarbonate (40 g) in THF (150 ml) was added dropwise. The mixture was stirred overnight. The aqueous phase was separated and washed with dietyl ether (2×100 ml). The combined organic phases were dried (anh. MgSO$_4$) and the solvents evaporated. The remaining product was stirred with diisopropyl ether and the precipitated product was filtered off. Yield of the title phenol derivative 5a: 24 g, mp: 187–189° C.

EXAMPLE 6 (Method a)

3-(4-Fluorophenyl)-1-[4-[4-[2-(2-propyloxy)phenyl]-1-piperidinyl]butan-1-yl]-2-imidazolidinone, Oxalate 6a To a solution of 1-(tert-Butyloxycarbonyl)-4-(2-hydroxyphenyl)piperidine 5a (5 g) in dry THF (100 ml) was added potassium tert-butoxide (2.2 g). After stirring for 5 minutes 2-iodopropane (9 g) was added and the mixture was refluxed for 3 hours. Additionally 1.1 g of potassium tert-butoxide was added and reflux was continued overnight. After cooling to room temperature inorganic salts were filtered off and the solvents evaporated in vacuo. The remaining oil was purified by filtering through silica gel (eluted with a 7:3 mixture of heptane and ethyl acetate). Yield: 4.5 g of 1-(tert-butyloxycarbonyl)-4-[2-(2-propyloxy)phenyl]piperidine all of which was dissolved in a mixture of dichloromethane (90 ml) and trifluoroacetic acid (40 ml). After stirring for one hour at room temperature all volatile material was evaporated in vacuo. To the remaining oil was added ethyl acetate (200 ml) and water (200 ml). pH was adjusted to >10 by addition of diluted aqueous NH$_4$OH. The organic phase was separated and washed with brine (2×50 ml). Work-up of the organic phase as above yielded 2.6 g of 4-[2-(2-propyloxy)phenyl]piperidine. A mixture of the thus isolated 1-unsubstituted piperidine (2.5 g), 1-(4-chloro-1-butyl)-3-(4-fluorophenyl)-2-imidazolidinone 2a (3.0 g), potassium carbonate (1.6 g), and potassium iodide (0.5 g) in MIBK (50 ml) was refluxed overnight. Inorganic salts were filtered off and MIBK evaporated in vacuo. The remaining crude product was purified by column chromatography on silica gel (eluted with 4% triethylamine in ethyl acetate). Pure title compound 6a crystallized from ethyl acetate. Yield: 2.6 g, mp: 130–131° C. $^1$H NMR (CDCl$_3$) δ 1.45 (d, 6H); 1.60 (t, 4H); 1.70–1.90 (m, 4H); 2.00–2.15 (m, 2H); 2.40 (t, 2H); 2.90–3.05 (m, 3H); 3.35 (t, 2H); 3.45 (t, 2H); 3.75 (t, 2H); 4.55 (h, 2H); 6.80–6.90 (m, 2H); 7.00 (t, 2H); 7.10 (dt, 1H); 7.15 (dd, 1H); 7.50 (dd, 2H).

In a similar way the following compounds were prepared:

3-Cyclohexyl-1-[4-[4-[2-(2-propyloxy)phenyl]-1-piperidinyl]butan-1-yl]-2-imidazolidinone, oxalate, 6b, mp: 138–141° C. (acetone). $^1$H NMR (DMSO-$d_6$): δ 0.95–1.20 (m, 1H), 1.20–1.40 (m, 4H), 1.30 (d, 6H), 1.40–1.80 (m, 9H), 1.80–2.00 (m, 4H), 2.90–3.20 (m, 7H), 3.25 (s, 4H), 3.40–3.60 (m, 3H), 4.65 (h, 1H), 6.90 (t, 1H), 7.00 (d, 1H), 7.10–7.25 (m, 2H).

3-Cyclohexyl-1-[3-[4-[2-(2-propyloxy)phenyl]-1-piperidinyl]-1-propyl]-2-imidazolidinone, oxalate, 6c, mp: 136–39° C. (acetone). $^1$H NMR (DMSO-d$_6$): δ 0.95–1.45 (m, 5H), 1.30 (d, 6H), 1.50–1.65 (m, 3H), 1.65–2.00 (m, 8H), 2.85–3.15 (m, 7H), 3.25 (s, 4H), 3.40–3.60 (m, 3H), 4.60 (h, 1H), 6.90 (t, 1H), 7.00 (d, 1H), 7.05–7.25 (m, 2H).

3-(2-Propyl)-1-[4-[4-[2-(2-propyloxy)phenyl]-1-piperidinyl]-1-butyl]-2-imidazolidinone, oxalate, 6d, mp: 82–4° C. (acetone). $^1$H NMR (DMSO-d$_6$): δ 1.05 (d, 6H), 1.25 (d, 6H), 1.40–1.55 (m, 2H), 1.55–1.75 (m, 2H), 1.80–2.00 (m, 4H), 2.90–3.15 (m, 7H), 3.15–3.30 (m, 4H), 3.40–3.60 (m, 2H), 3.90 (h, 1H), 4.60 (h, 1H), 6.90 (t, 1H), 7.00 (d, 1H), 7.05–7.25 (m, 2H).

3-Cyclohexyl-1-[6-[4-[2-(2-propyloxy)phenyl]-1-piperidinyl]-1-hexyl]-2-imidazolidinone, oxalate, 6e, mp: 77–9° C. (acetone). $^1$H NMR (DMSO-d$_6$): δ 0.95–1.50 (m, 14H), 1.25 (d, 6H), 1.50–1.80 (m, 6H), 1.80–2.00 (m, 4H), 2.80–3.15j (m, 7H), 3.15–3.25 (m, 4H), 3.35–3.60 (m, 3H), 4.60 (h, 1H), 6.90 (t, 1H), 7.00 (d, 1H), 7.05–7.25 (m, 2H).

3-Cyclohexyl-1-[4-[4-[2-(cyclopropylmethoxy)phenyl]-1-piperidinyl]butan-1-yl]-2-imidazolidinone, oxalate, 6f, mp: 186–93° C. (ethyl acetate). $^1$H NMR (DMSO-d$_6$): δ 0.25–0.40 (m, 2H), 0.60–0.70 (m, 2H), 0.95–1.15 (m, 1H), 1.20–1.45 (m, 5H), 1.50–1.90 (m, 9H), 1.95–2.10 (m, 2H), 2.10–2.35 (m, 2H), 2.85 (t, 2H), 3.05–3.25 (m, 3H), 3.20 (t, 2H), 3.25–3.35 (m, 4H), 3.55–3.85 (m, 3H), 3.80 (d, 2H), 6.80 (d, 1H), 6.90 (t, 1), 7.10–7.25 (m, 2H).

3-Cyclohexyl-1-[4-[4-[2-(2,2-dimethyl-1-propyloxy) phenyl]-1-piperidinyl]butan-1-yl]-2-imidazolidinone oxalate, 6g, mp: 162–68° C. (ethyl acetate/acetone). $^1$H NMR (DMSO-d$_6$): δ 1.05 (s, 9H), 1.15–1.85 (m, 14H), 1.80–2.05 (m, 4H), 2.85–3.15 (m, 7H), 3.20 (s, 4H), 3.35–3.60 (m, 3H), 3.65 (s, 2H), 6.85–7.00 (m, 2H), 7.05–7.25 (m, 2H).

By an analogous method, but applying mesylates 3a and 3b instead of chlorides as alkylating reagents the following derivatives were prepared:

3-Cyclohexyl-1-[4-[4-[2-(2-propyloxy)phenyl]-1-piperidinyl]butan-1-yl]-1,3-dihydroimidazol-2-one, oxalate, 6h, mp: 68–71° C. (acetone). $^1$H NMR (DMSO-d$_6$): δ 1.05–1.55 (m, 5H), 1.30 (d, 6H), 1.55–1.85 (m, 9H), 1.85–2.00 (m, 4H), 2.90–3.20 (m, 5H), 3.40–3.60 (m, 4H), 3.75 (dt, 1H), 4.65 (h, 1H), 6.50 (d, 1H), 6.55 (d, 1H), 6.90 (t, 1H), 7.00 (d, 1H), 7.10–7.25 (m, 2H).

3-(1-Adamantyl)-1-[4-[4-[2-(2-propyloxy)phenyl]-1-piperidinyl]butan-1-yl]-1,3-dihydroimidazol-2-one, oxalate, 6i, mp: 116–22° C. (ethyl acetate/acetone). $^1$H NMR (DMSO-d$_6$): δ 1.30 (d, 6H), 1.50–1.75 (m, 10H), 1.75–2.10 (m, 4H), 2.00–2.20 (m, 9H), 2.85–3.20 (m, 5H), 3.35–3.60 (m, 4H), 4.65 (h, 1H), 6.50 (s, 2H), 6.90 (t, 1H), 7.00 (d, 1H), 7.05–7.25 (m, 2H).

EXAMPLE 7 (Method a)

3-(4-Fluorophenyl)-1-[4-[4-[2-(2-trifluoromethylsulfonyloxy)phenyl]-1-piperidinyl] butan-1-yl]-2-imidazolidinone 7a A solution of 1-(tert-butyloxycarbonyl)-4-(2-hydroxyphenyl)piperidine 5a (9 g) and triethylamine (7 ml) in dichloromethane (90 ml) was cooled to 5° C. and a solution of trifluoromethansulfonic acid anhydride (10 ml) in dichloromethane (15 ml) was added dropwise. After stirring for one hour at room temperature water (200 ml) was added. The organic phase was separated and worked-up as previously. Yield of crude 1-(tert-butyloxycarbonyl)-4-(2-trifluoromethylsulfonyloxyphenyl)piperidine: 14 g. The 1-(tertbutyloxycarbonyl) N-protection group was splitted off as in Example 5 yielding 9 g of crude 4-(2-trifluoromethylsulfonyloxyphenyl)piperidine. A mixture of the thus isolated 1-unsubstituted piperidine (5.5 g), 1-(4-chloro-1-butyl)-3-(4-fluorophenyl)-2-imidazolidinone 2a (4.0 g), and potassium iodide (0.5 g) in MIBK (80 ml) was refluxed overnight. MIBK was evaporated in vacuo. The remaining oil was dissolved in ethyl acetate (100 ml) and water (100 ml) and pH was adjusted to >9 by addition of diluted aqueous NH$_4$OH. The organic phase was separated and worked-up as previously. The remaining crude product was purified by column chromatography on silica gel (eluted with 4% triethylamine in a 9:1 mixture of ethyl acetate and ethanol). Pure title compound 7a crystallized from a 1:1 mixture of diethyl and diisopropyl ether. Yield: 2.0 g, mp: 77–79° C. $^1$H NMR (CDCl$_3$) δ 1.55–1.70 (m, 4H); 1.70–1.85 (m, 4H); 2.05 (dt, 2H); 2.40 (t, 2H); 2.80–2.95 (m, 1H); 3.05 (d, 2H); 3.35 (t, 2H); 3.45 (t, 2H); 3.80 (t, 2H); 7.00 (t, 2H); 7.20–7.45 (m, 4H); 7.50 (dd, 2H).

In a similar way the following trifluoromethylsulfonyloxy derivatives were prepared:

3-Cyclohexyl-1-[4-[4-[2-(2-trifluoromethylsulfonyloxy) phenyl]-1-piperazinyl]butan-1-yl]-2-imidazolidinone, hydrochloride 7b, mp: 153–154° C. (acetone). $^1$H NMR (DMSO-d$_6$) δ 1.00–1.75 (m, 14H); 3.00–3.55 (m, 17H); 7.25–7.50 (m, 4H); 11.20 (s, 1H).

3-(4-Fluorophenyl)-1-[4-[4-[2-(2-trifluoromethylsulfonyloxy)phenyl]-1-piperazinyl] butan-1-yl]-2-imidazolidinone, 7c, mp: 68–70° C. (diisopropyl ether). $^1$H NMR (CDCl$_3$) δ 1.55–1.65 (m, 4H); 2.45–2.55 (m, 2H); 2.65 (broad s, 4H); 3.05 (t, 4H); 3.35 (t, 2H); 3.50 (t, 2H); 3.80 (t, 2H); 7.00–7.20 (m, 5H); 7.35 (dt, 1H); 7.50 (dd, 2H).

EXAMPLE 8

4-[2-(2-Propyloxy)phenyl]-1,2,3,6-tetrahydropyridine 8a

2-Bromophenol (10 g), 2-bromopropane (7.1 g), potassium carbonate (12 g), and a potassium iodide crystal were refluxed in MIBK (100 ml) for 6 hours. Inorganic salts were filtered off and MIBK evaporated in vacuo. Ice cooled water and diethyl ether (200 ml) were added and pH adjusted to >10 by adding diluted aqueous NaOH. The organic phase was separated and worked-up as above. Yield of 2-bromophenyl 2-propyl ether (11 g) as an oil. To diethyl ether (38 ml) cooled below –10° C. was added a 1.6 M solution of n-butyl lithium in hexane (31 ml). The resulting solution was cooled to –50° C. and all off the 2-bromophenyl 2-propyl ether from above in diethyl ether (20 ml) was added dropwise. After stirring for another 20 minutes at –50° C. a solution of 1-benzyl-4-piperidone (9.7 g) in diethyl ether (25 ml) was added dropwise at –50° C. The mixture was allowed gradually to heat to –10° C. and poured into diluted aqueous hydrochloric acid. The organic phase was discarded and diluted aqueous NH$_4$OH was added until pH>9. Extraction with diethyl ether (2×200 ml) and work-up of the organic phase as above yielded the 1-benzyl-4-hydroxy-4-[2-(2-propyloxy)phenyl]piperidine (13.7 g) as an oil. All of the hydroxypiperidine was refluxed in trifluoroacetic acid (100 ml) for 2.5 hours. Ice (1000 g) and diethyl ether (300 ml) were added and pH was adjusted to >9 by addition of diluted aqueous NH₄OH. After extraction several times (3×200 ml) with diethyl ether, the combined organic phases were worked-up as previously. The crude product was purified by column chromatography on silica gel (eluted with 4% triethylamine in a 3:1 mixture of heptane and ethyl acetate). Yield: 4.2 g as an oil. To all of the thus obtained 1-benzyl-4-[2-(2-propyloxy)phenyl]-1,2,3,6-tetrahydropyridine in 1,1,1-trichloroethane (40 ml) was added dropwise a solution of 2,2,2-trichloroethyl chloroformate (2,2 ml) in trichloroethane (10 ml) at reflux temperature. After reflux for 1.5 hours the solvent was evaporated. The crude product was filtered through silica gel (eluted with ethyl acetate/heptane 1:3) affording 4.5 g of the pure 2,2,2-trichloroethyl carbamate derivative as an oil. All of this carbamate was dissolved in acetic acid (40 ml). Water was added and at 40–50° C. Zn powder (8 g) was added in small portions during 10 minutes. After stirring for 2 hours at 50° C. inorganic salts were filtered off and the solvents were evaporated in vacuo. Ice and ethyl acetate were added and pH adjusted to >9 by addition of diluted aqueous NH₄OH. The organic phase was separated and worked-up as above yielding 2.5 g of the title compound 8a as an oil.

EXAMPLE 9

3-Cyclohexyl-1-[4-[4-[2-(2-propyloxy)phenyl]-1,2,3,6-tetrahydropyridin-1-yl]butan-1-yl]-2-imidazolidinone Oxalate 9a A mixture of 4-[2-(2-propyloxy)phenyl]-1,2,3,6-tetrahydropyridine 8a (2.3 g), 1-(4-chloro-1-butyl)-3-cyclohexyl-2-imidazolidinone 1a (1.25 g), potassium carbonate (1.6 g) and a potassium iodide crystal in MIBK (60 ml) was refluxed overnight.

Inorganic salts were filtered off and the solvent was evaporated in vacuo. The crude title compound 9a was purified by column chromatography on silica gel (eluted with 4% triethylamine in a 3:1 mixture of ethyl acetate and heptane). Yield: 1 g as an oil. The oxalate salt crystallized from 2-propanol, mp: 131–133° C.

In a similar way the following tetrahydropyridinyl derivatives were prepared:

3-(4-Fluorophenyl)-1-[4-[4-[2-(2-propyloxy)phenyl]-1,2,3,6-tetrahydropyridin-1-yl]butan-1-yl]-2-imidazolidinone oxalate 9b, mp 150–2° C. (acetone). ¹H NMR (DMSO-d₆): δ 1.25 (d, 6H), 1.45–1.65 (m, 2H), 1.65–1.80 (m, 2H), 2.60–2.80 (m, 2H), 3.10 (t, 2H), 3.20 (t, 2H), 3.20–3.35 (m, 2H), 3.45 (t, 2H), 3.65–3.90 (m, 4H), 4.60 (h, 1H), 5.65–5.80 (m, 1H), 6.90 (t, 1H), 7.00 (d, 1H), 7.05–7.20 (m, 3H), 7.25 (t, 1H), 7.50–7.65 (m, 2H).

3-Cyclohexyl-1-[4-[4-[2-(cyclopropylmethoxy)phenyl]-1,2,3,6-tetrahydropyridin-1-yl]butan-1-yl]-2-imidazolidinone 9c, colorless oil. ¹H NMR (CDCl₃): δ 0.25–0.45 (m, 2H), 0.50–0.75 (m, 2H), 0.90–1.00 (m, 1H), 1.00–1.95 (m, 14H), 2.50 (t, 2H), 2.55–2.75 (m, 4H), 3.05–3.15 (m, 2H), 3.20 (t, 2H), 3.25 (s, 4H), 3.30 (dt, 1H), 3.80 (d, 2H), 5.75–5.80 (m, 1H), 6.80 (d, 1H), 6.90 (t, 1H), 7.10–7.30 (m, 2H).

By an analogous method, but applying mesylates 3a and 3b instead of chlorides as alkylating reagents the following derivatives were prepared:

3-Cyclohexyl-1-[4-[4-[2-(2-propyloxy)phenyl]-1,2,3,6-tetrahydropyridin-1-yl]butan-1-yl]-2,3-dihydroimidazol-2-one 9d, colorless oil. ¹H NMR (CDCl₃): δ 1.10–1.50 (m, 5H), 1.30 (d, 6H), 1.50–1.75 (m, 5H), 1.75–2.00 (m, 4H), 2.45 (t, 2H), 2.50–2.60 (m, 2H), 2.60–2.68 (m, 2H), 3.05–3.15 (m, 2H), 3.65 (t, 2H), 3.90–4.05 (m, 1H), 4.50 (h, 1H), 5.70–5.75 (m, 1H), 6.20 (d, 1H), 6.25 (d, 1H), 6.90 (t, 2H), 7.10–7.25 (m, 2H).

3-(1-Adamantyl)-1-[4-[4-[2-(2-propyloxy)phenyl]-1,2,3,6-tetrahydropyridin-1-yl]butan-1-yl]-2,3-dihydroimidazol-2-one oxalate 9e, mp: 104–9° C. (ethyl acetate/acetone). ¹H NMR (DMSO-d₆): δ 1.25 (d, 6H), 1.50–1.75 (m, 10H), 2.00–2.20 (m, 9H), 2.60–2.80 (m, 2H), 3.00–3.20 (m, 2H), 3.30 (t, 2H), 3.50 (t, 2H), 3.70–3.85 (m, 2H), 4.60 (h, 1H), 5.70–5.80 (m, 1H), 6.50 (s, 2H), 6.90 (t, 1H), 7.00 (d, 1H), 7.15 (d, 1H), 5.75 (t, 1H).

EXAMPLE 10 (Method c)

3-Cyclohexyl-1-[4-[4-[2-(1,1-dimethylethoxy)phenyl]-1-piperidinyl]butan-1-yl]-2-imidazolidinone Oxalate, 10a A solution of 3-cyclohexyl-1-[4-[4-(2-hydroxyphenyl)-1-piperidinyl]butan-1-yl]-2-imidazolidinone (1 g, prepared from 4-(2-hydroxyphenyl)piperidine (described in Example 5) and 1a by the method described in Example 4) in dry methylene chloride (10 ml) was cooled to −20° C. Isobutylene (5 ml, condensed at −25° C.) was added under a nitrogen atmosphere followed by addition of trifluoromethanesulfonic acid (0.4 ml). The mixture was stirred for 3 h at −20° C. followed by addition of triethylamine (2 mL). After warming to room temperature the reaction mixture was concentrated in vacuo followed by addition of 2 M ammonia and extraction with methylene chloride. The organic phase was dried over magnesium sulfate and concentrated in vacuo leaving an oil which was purified by flash chromatography (silica gel, eluent: ethyl acetate/MeOH/triethylamine 97:2:1). The resulting colorless oil was dissolved in a mixture of ethyl acetate and acetone. Addition of oxalic acid gave the title compound, 10a, as a crystalline material. Yield: 0.8 g, mp: 147–53° C. ¹H NMR (DMSO-d₆): δ 0.95–2.10 (m, 18H), 1.35 (s, 9H), 2.85–3.15 (m, 7H), 3.25 (s, 4H), 3.35–3.60 (m, 3H), 6.90–7.25 (m, 4H).

Pharmacology

The compounds of Formula I have been tested according to well established and reliable pharmacological methods for determination of the activity at the 5-HT$_{1A}$ and the D$_2$ receptor, repectively, and for cataleptogenic effects. The tests were as described in the following.

Inhibition of ³H8-OH-DPAT Binding to Serotonin 5-HT$_{1A}$ Receptors in Rat Brain in vitro By this method the inhibition by drugs of the binding of the 5-HT$_{1A}$ agonist 3H-8-OH-DPAT (1 nM) to 5-HT$_{1A}$ receptors in membranes from rat brain minus cerebellum is determined in vitro. Accordingly, this is a test for affinity for the 5-HT$_{1A}$ receptor. The test was performed as described by Hyttel et al., *Drug Dev. Res.* 1988, 15, 389–404.

Inhibition of 3H-spiroperidol Binding to Dopamine D$_2$ Receptors in Rat Brain in vitro By this method the inhibition by drugs of the binding of the D$_2$ antagonist ³H-spiroperidol (0.5 nM) to D$_2$ receptors in membranes from rat corpus striatum is determined in vitro. Accordingly, this is a test for affinity for the dopamine D$_2$ receptor. This method is described in detail in J.Hyttel et al, *J. Neurochem.*, 1985, 44, 1615. The results of the binding assays are given in Table 1.

TABLE 1

Binding Data (IC$_{50}$ values in nM)

| Compound No | $^3$H 8-OH DPAT (5-HT$_{1A}$) | $^3$H Spiroperidole (D$_2$) |
|---|---|---|
| 4a | 1.8 | 6.4 |
| 4b | 2.2 | 3.9 |
| 4c | 5.4 | 13. |
| 4d | 4.0 | 15. |
| 4e | 40. | 24. |
| 6a | 4.8 | 7.9 |
| 6b | 5.4 | 8.7. |
| 6c | 35. | 110. |
| 6d | 5. | 7.7 |
| 6e | 20. | 16. |
| 6f | 26. | 37. |
| 6h | 4.1 | 10. |
| 7a | 37. | 41. |
| 7b | 42. | 49. |
| 7c | 15. | 57. |
| 9a | 9. | 8.7 |
| 9b | 2.8 | 11. |
| 9d | 26. | 27. |
| buspirone | 41. | 250. |
| haloperidol | 3200. | 7.5 |

Cataleptogenic Effect

Evaluation of cataleptogenic effects of the compounds of the invention was made according to the method of Sanchez, C. et al.; *Drug Dev. Res.* 1991, 22, 239–250. Examples of compounds tested are shown in Table 2

TABLE 2

(ED$_{50}$ values in µmol/kg)

| Compound No | Catalepsy (1–6 h, sc) |
|---|---|
| 4a | >38 |
| 4b | >44 |
| 4c | >37 |
| 4d | >42. |
| 4e | >34 |
| 6a | >44 |
| 6b | >38 |
| 6d | >41 |
| 6e | >33 |
| 6h | >38 |
| 7b | >35 |
| 7c | >37 |
| 9a | >38 |
| 9b | >37 |
| haloperidol | 0.36 |

Furthermore, the compounds of the present invention were tested with respect to their ability to inhibit 5-MeO-DMT-induced 5-HT syndrome in rats. 5-Methoxy-N,N-dimethyltryptamine (5-MeO DMT) is a 5-HT$_{1A}$ agonist. Partiel 5-HT$_{1A}$ agonists such as buspirone inhibit the characteristic 5-HT syndrome produced by 5-MeO DMT. Accordingly, the said test is a test for determining the antagonist effects of a test compound on 5-HT$_{1A}$ receptors in vivo. The test was performed as described in Smith L. M. and Peroutka S. J., *Pharmacol. Biochem. Behav.*, 1986, 24, 1513–1519. The compounds of the present invention were active in this test model.

The compounds were also tested in the Methylphenidate test as published by Pedersen and Christensen in Acta Pharmacol. et Toxicol. 31, 488–496 (1972) and in the Pergolide Rotation Test as published by Arnt, J. and Hyttel, J., *J. Neural. Transm.* 1986, 67, 225–240. Both these testmodels are in vivo tests for antidopaminergic activity. Some of the compounds of the invention also showed effects in these test models.

As seen from the above, the compounds of the invention show affinity for both 5-HT$_{1A}$ and dopamine D$_2$ receptors in vivo. Furthermore, they showed 5-HT$_{1A}$ receptor agonistic effect in vivo whereas they did not have cataleptogenic effects. Finally, some of the compounds also showed dopamine D$_2$ antagonistic effects in vivo. Accordingly, the compounds have a combination of effects at the said two receptors, i.e. acting as agonists, partial agonists or antagonists at the 5-HT$_{1A}$ receptor and blocking the dopamine D$_2$ receptor without showing cataleptogenic. Drugs having such properties are useful in the treatment the psychic disorders as mentioned previously. They are in particular considered useful in the treatment of psychosis, including positive symptoms of schizophrenia.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of Compound 4a calculated as the free base:

| | |
|---|---|
| Compound 4a | 5.0 mg |
| Lactose | 60. mg |
| Maize starch | 30. mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of Compound 4a calculated as the free base:

| | |
|---|---|
| Compound 4a | 0.5 mg |
| Lactose | 46.9 mg |
| Maize starch | 23.5 mg |
| Povidone | 1.8 mg |
| Microcrystalline cellulose | 14.4 mg |

-continued

| | |
|---|---|
| Croscarmellose Sodium Type A | 1.8 mg |
| Magnesium stearate | 0.63 mg |

3) Syrup containing per milliliter:

| | |
|---|---|
| Compound 4b | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |

4) Solution for injection containing per milliliter:

| | |
|---|---|
| Compound 6b | 0.5 mg |
| Sorbitol | 5.1 mg |
| Acetic acid | 0.08 mg |
| Water for injection | ad 1 ml |

What is claimed is:

1. A 4-phenylpiperidine and 4-phenyl-1,2,3,6-tetrahydropyridine compound having Formula 1:

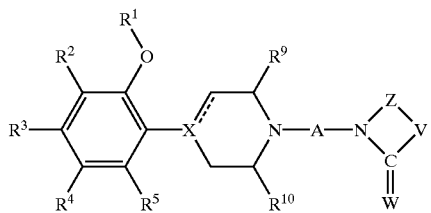

wherein A is a spacer group selected from the group consisting of $C_{3-8}$ alkylene, $C_{3-8}$ alkenylene, $C_{3-8}$ alkynylene, and $C_{3-7}$ cycloalkylene, said spacer group being optionally substituted with lower alkyl, phenyl or hydroxy; wherein said alkylene, alkenylene and alkynylene groups can be branched or straight chains, $R^1$ is branched $C_{3-10}$ alkyl, branched $C_{3-10}$ alkenyl, branched $C_{3-10}$ alkynyl, cycloalk(en)yl, cycloalk(en)yl-lower alk(en/yn)yl, trifluoromethylsulfonyl, or lower alkylsulfonyl, $R^2$–$R^5$ are independently selected from the group consisting of hydrogen, halogen, lower alkyl, lower alkoxy, lower alkylthio, hydroxy, lower alkylsulfonyl, cyano, lower alkylcarbonyl, phenylcarbonyl, halogen substituted phenylcarbonyl, trifluoromethyl, trifluoromethylsulfonyloxy, cycloalkyl, cycloalkyl-lower alkyl, nitro, lower alkylamino, di-lower-alkylamino and trifluoromethylthio, $R^9$ and $R^{10}$ are independently selected form the group consisting of hydrogen, and lower alkyl;

W is O;

V is $NR^8$ wherein $R^8$ is independently selected from the group consisting of hydrogen, lower alkyl, lower alkenyl, cycloalkyl, cycloalkyl-lower-alkyl, phenyl-lower alkyl and phenyl;

Z is —$(CH_2)_m$—, m being 2 or Z is —CH=CH—;

X is C;

any alkyl, cycloalkyl or cycloalkylalkyl group present can be optionally substituted with one or two hydroxy groups, which can be optionally esterified with an aliphatic or phenyl carboxylic acid; and any phenyl substituent present can be optionally substituted with halogen, lower alkyl, lower alkoxy, lower alkylthio, hydroxy, lower alkylsulfonyl, cyano, phenylcarbonyl, $C_{1-8}$ alkylcarbonyl, N'-($C_{1-18}$)alkylcarbonyl or N',N'-di ($C_{1-18}$)alkylcarbonyl, trifluoromethyl, trifluoromethylsulfonyloxy, cycloalkyl, cycloalkylalkyl or nitro;

or a pharmaceutically acceptable acid addition salt thereof.

2. The compound of claim 1, wherein A is a —$(CH_2)_n$— group wherein n is an integer from 3–8, inclusive.

3. The compound of claim 2, wherein n is 4–6.

4. The compound of claim 1, wherein $R^1$ is branched $C_{3-6}$ alkyl, cycloalkyl, cycloalkyl-lower alkyl or trifluoromethylsulfonyl.

5. The compound of claim 4, wherein $R^1$ is 2-propyl, 2-methyl-1-propyl, 2-butyl, 3-pentyl, 2,2-dimethyl-1-propyl, tert-butyl, cyclopentyl, cyclopropylmethyl, 2,4-dimethyl-3-pentyl or trifluoromethylsulfonyl.

6. The compound of claim 1, wherein $R^2$–$R^5$ are independently hydrogen, halogen or cyano.

7. The compound of claim 5, wherein $R^2$–$R^5$ are all hydrogen.

8. The compound of claim 1, wherein $R^9$ and $R^{10}$ are both hydrogen.

9. The compound of claim 1, wherein $R^8$ is lower alkyl, cycloalkyl, phenyl or phenyl substituted with halogen.

10. The compound of claim 3, wherein n is 4.

11. The compound of claim 5, wherein one of $R^2$–$R^5$ is halogen and the others are hydrogen.

12. A pharmaceutical composition comprising at least one compound of claim 1 in a therapeutically effective amount and in combination with one or more pharmaceutically acceptable carriers or diluents.

* * * * *